(12) United States Patent
Nakagawa et al.

(10) Patent No.: US 6,749,732 B2
(45) Date of Patent: Jun. 15, 2004

(54) RAPID RESPONSE STRUCTURE OF GAS SENSOR

(75) Inventors: Kazuya Nakagawa, Kariya (JP); Kazuhiro Okazaki, Aichi-ken (JP)

(73) Assignee: Denso Corporation (JP)

( * ) Notice: Subject to any disclaimer, the term of this patent is extended or adjusted under 35 U.S.C. 154(b) by 41 days.

(21) Appl. No.: 10/084,162

(22) Filed: Feb. 28, 2002

(65) Prior Publication Data

US 2004/0011646 A1 Jan. 22, 2004

(30) Foreign Application Priority Data

Feb. 28, 2001 (JP) ........................................ 2001-054327
Nov. 8, 2001 (JP) ........................................ 2001-343724

(51) Int. Cl.$^7$ ............................................ G01N 27/407
(52) U.S. Cl. ........................................ 204/428; 204/424
(58) Field of Search .................................. 204/421–429

(56) References Cited

U.S. PATENT DOCUMENTS

| 3,891,529 | A | * | 6/1975 | Beesch |
| 4,929,331 | A | * | 5/1990 | Kato et al. |
| 5,707,504 | A | * | 1/1998 | Jyouno et al. |
| 5,762,771 | A | | 6/1998 | Yamada et al. |
| 6,279,376 | B1 | | 8/2001 | Yamada et al. |
| 6,346,179 | B1 | * | 2/2002 | Makino et al. |
| 6,348,141 | B1 | * | 2/2002 | Kato et al. |

FOREIGN PATENT DOCUMENTS

| JP | 9-210954 | 8/1997 |
| JP | 9-222416 | 8/1997 |
| JP | 11-183425 | 7/1999 |
| JP | 2000-171429 | 6/2000 |

\* cited by examiner

*Primary Examiner*—Kaj K. Olsen
(74) *Attorney, Agent, or Firm*—Nixon & Vanderhye PC (57) ABSTRACT

A rapid response structure of a gas sensor which includes a protective cover assembly defining therein a gas chamber to which a gas to be measured is admitted. The gas assembly consists of an outer and an inner cover. The inner cover is disposed within the outer cover with a clearance which defines a gas path extending from gas inlet holes formed in the outer cover to the gas chamber through gas inlet holes formed in the inner cover. The outer and inner covers are so designed geometrically as to minimize the interference of a return gas flow produced within the clearance with the flow of the gas into the gas chamber, thereby facilitating the entrance of the gas into the gas chamber.

12 Claims, 10 Drawing Sheets

RAPID RESPONSE STRUCTURE OF GAS SENSOR

BACKGROUND OF THE INVENTION

1. Technical Field of the Invention

The present invention relates generally to a gas sensor which may be installed in an exhaust system of an internal combustion engine to determine the concentration of $O_2$, an air-fuel ratio, or the concentration of NOx in exhaust emissions, and more particularly to an improved structure of such a type of gas sensor designed to ensure a rapid response to a change in, for example, concentration of a gas to be measured.

2. Background Art

Conventionally, gas sensors are used for burning control of internal combustion engines for automotive vehicles. As a typical example, a gas sensor is installed in an exhaust pipe of an automotive engine to measure the concentration of a specified gas contained in exhaust emission of the engine. A gas sensor of this type consists essentially of a gas sensor element disposed within a hollow cylindrical housing, an air cover installed on a base portion of the housing, and a gas cover assembly installed on a tip portion of the housing which is made up of an outer cover and an inner cover.

Figure 16:
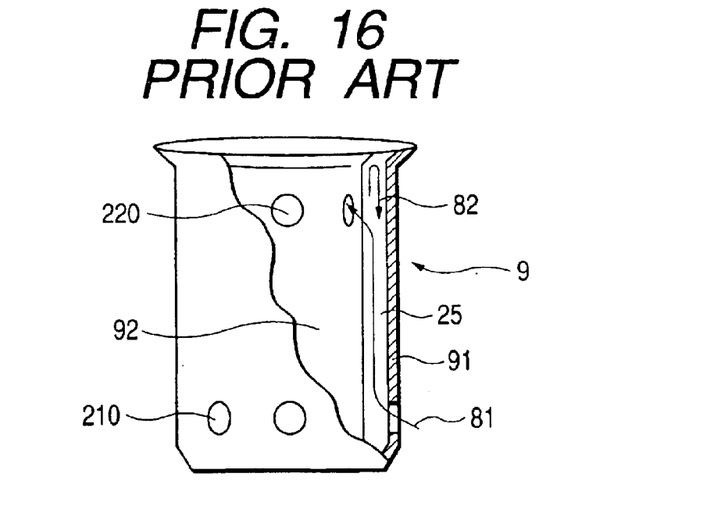
FIG. 16 is a partially sectional view which shows an internal structure of a protective cover assembly installed in a conventional gas sensor.
Figure 17:
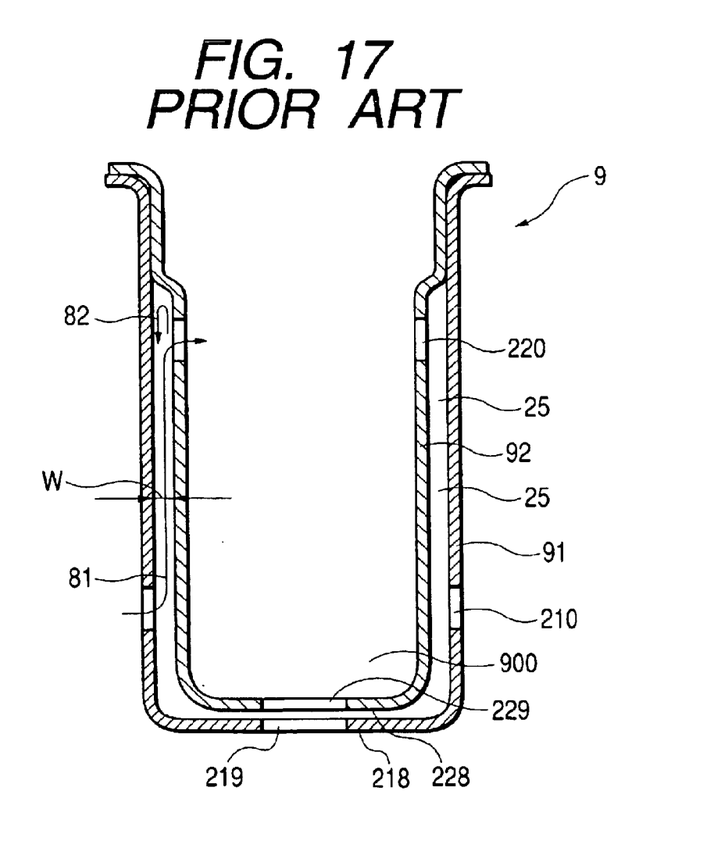
FIG. 17 is a longitudinal sectional view of FIG. 16.

FIGS. 16 and 17 show an example of such a gas cover assembly. The gas cover assembly 9 is made up of an outer cover 91 and an inner cover 92. The inner cover 92 defines therein a gas chamber 900 into which a gas to be measured is admitted through gas inlet holes 210 and 220. The gas inlet holes 220 formed in the inner cover 92 are located closer to a base portion of the gas sensor (i.e., an upper side of the drawings) than the gas inlet holes 210 formed in the outer cover 91. The gas to be measured first enters the gas inlet holes 210 of the outer cover 91, creates an upward flow 81, as indicated by an arrow in each drawing, within a clearance 25 between the covers 91 and 92, and then enters the gas chamber 900 through the gas inlet holes 220 of the inner cover 92.

The above structure, however, encounters the drawback in that a portion of the gas not admitted into the gas inlet holes 220 returns on an upper end of the clearance 25, as viewed in the drawings, downwards, forming a return flow toward the upstream end of the clearance 25, which disturbs entrance of the gas into the gas chamber 900 through the gas inlet holes 220. This results in a time lag between measurement of, for example, the concentration of the gas admitted into the gas chamber 900 and a change in concentration of a gas existing outside the cover assembly 9, thus leading to a decrease in response rate of the gas sensor.

SUMMARY OF THE INVENTION

It is therefore an object of the invention to provide an improved structure of a gas sensor designed to ensure a rapid response to a change in, for example, concentration of a gas to be measured.

According to one aspect of the invention, there is provided a gas sensor which may be employed in measuring the concentration of a specified gas contained in exhaust emission of an internal combustion engine of an automotive vehicle. The gas sensor has a length with a first and a second end opposed to each other and comprises: (a) a hollow cylindrical housing having a first end and a second end opposed to the first and second ends of the gas sensor, respectively; (b) a sensing element retained within the housing which has a length extending in a longitudinal direction of the gas sensor, including a sensing portion working to measure a concentration of a specified gas; and (c) a cover assembly installed on the second end of the housing to define a gas chamber in which the sensing portion of the sensing element is disposed and into which the specified gas is admitted. The cover assembly has a length extending in the longitudinal direction of the gas sensor and includes an outer and an inner cover. The outer cover has a first gas inlet hole formed in a side wall thereof. The inner cover has formed in a side wall thereof a second gas inlet hole which is located closer to the first end of the gas sensor than the first gas inlet hole of the outer cover. The inner cover is disposed within the outer cover with a given clearance between the outer and inner covers. At least one of the outer and inner covers is geometrically designed to define a gas path within the clearance which establishes a flow of the specified gas from the first gas inlet hole to the gas chamber through the second gas inlet hole for minimizing the interference of a return gas flow produced within the clearance, oriented toward the first gas inlet hole with the flow of the specified gas into the gas chamber along the gas path. This facilitates ease of the entrance of the flow of the specified gas into the gas chamber, thereby ensuring a rapid response of an output of the gas sensor to a change in concentration of the specified gas.

In the preferred mode of the invention, one of the outer and inner covers of the cover assembly has formed on the side wall thereof a shoulder which separates the clearance between the outer and inner covers into a wider and a narrower portion.

The wider portion is preferably 1.1 times wider than the narrower portion.

The wider portion is located around the second gas inlet hole of the inner cover.

The inner cover may have a gas flow-opposed wall oriented upstream of the gas path. The second gas inlet hole may be formed in the gas flow-opposed wall.

The gas flow-opposed wall may be defined by a shoulder which is formed on the side wall of the inner cover and extends outward to the first end of the gas sensor.

A groove may also be formed in the side wall of the outer cover serving to direct the flow of the specified gas to the second gas inlet hole of the inner cover.

According to the second aspect of the invention, there is provided a gas sensor having a length with a first and a second end opposed to each other which comprises: (a) a hollow cylindrical housing having a first end and a second end opposed to the first and second ends of the gas sensor, respectively; (b) a sensing element retained within the housing which has a length extending in a longitudinal direction of the gas sensor, including a sensing portion working to measure a concentration of a specified gas; and (c) a cover assembly installed on the second end of the housing to define a gas chamber in which the sensing portion of the sensing element is disposed and into which the specified gas is admitted. The cover assembly has a length extending in the longitudinal direction of the gas sensor and includes an outer and an inner cover. The outer cover has a first gas inlet hole formed in a side wall thereof. The inner cover has a tapered surface formed on a side wall thereof which tapers off to a side of the second end of the gas sensor. The inner cover has formed in the tapered surface thereof a second gas inlet hole which is located closer to the first end of the gas sensor than the first gas inlet hole of the outer cover. The inner cover is disposed within the outer cover with a given clearance between the outer and inner covers which defines a gas path establishing a flow of the specified gas from the first gas inlet hole to the gas chamber through the second gas inlet hole. The tapered surface geometrically serves to minimize the interference of a return gas flow produced within the clearance, oriented toward the first gas inlet hole with the flow of the specified gas into the gas chamber along the gas path.

In the preferred mode of the invention, the outer cover has formed on the side wall thereof a surface which tapers off to a side of the first end of the gas sensor to define a wider portion of the clearance between the tapered surface of the inner cover and the tapered surface of the outer cover.

The inner cover has a straight surface continuing from the tapered surface, extending straight in the longitudinal direction of the gas sensor.

A groove may also be formed in the side wall of the outer cover serving to direct the flow of the specified gas to the second gas inlet hole of the inner cover.

The outer cover may have a shoulder formed closer to an upstream side of the flow of the specified gas than the tapered surface of the inner cover to define an upstream portion of the gas path closer to the first gas inlet hole of the outer cover and a downstream portion of the gas path closer to the second gas inlet hole of the inner cover. The downstream portion is greater in area than the upstream portion in a direction traversing the longitudinal direction of the gas sensor.

A groove may also be formed in a portion of the side wall of the outer cover closer to the first gas inlet hole than the shoulder of the outer cover. The groove serves to direct the flow of the specified gas to the second gas inlet hole of the inner cover.

The groove may have a length extending in alignment with the second gas inlet hole of the inner cover in the longitudinal direction of the gas sensor.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
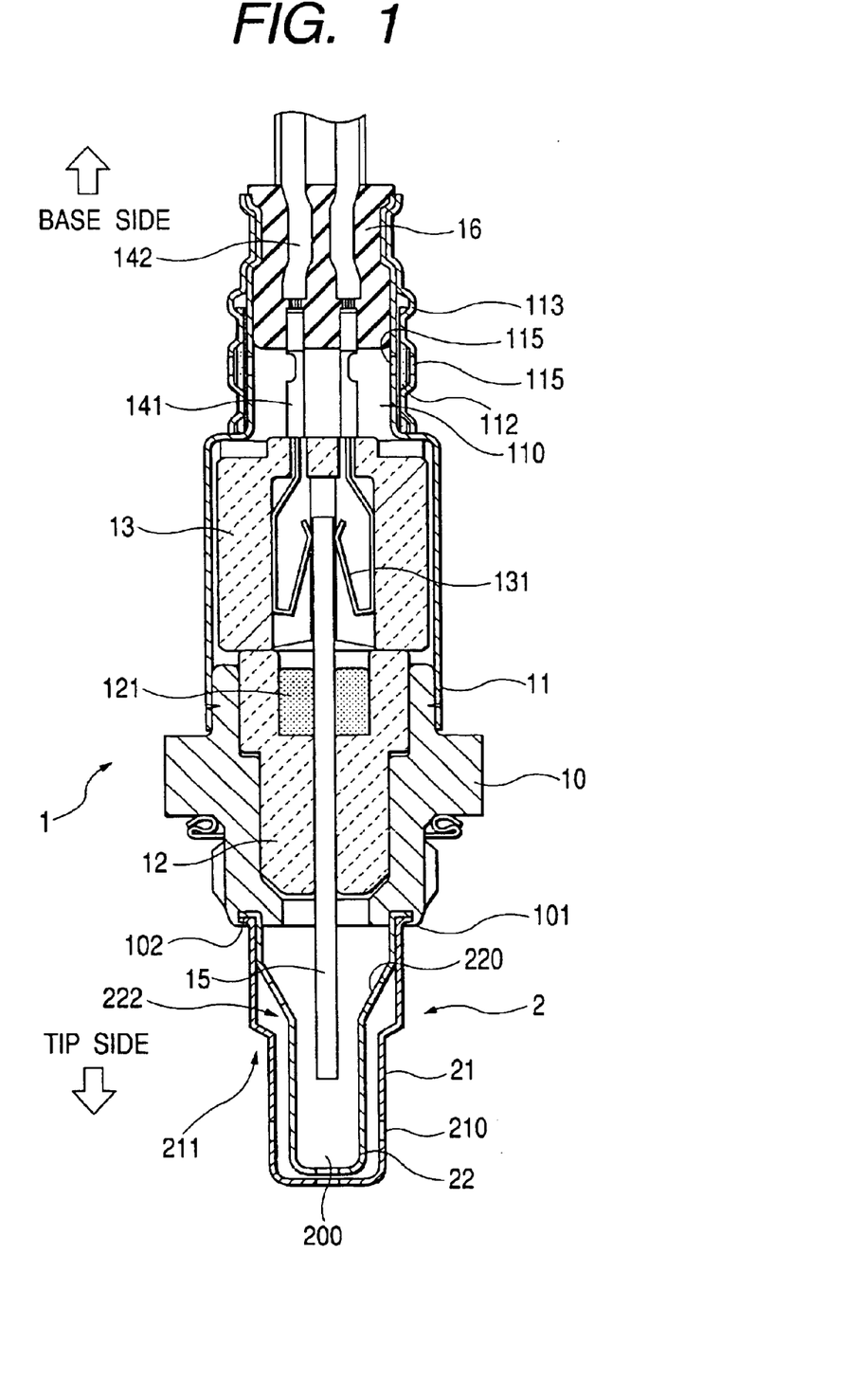
FIG. 1 is a longitudinal sectional view which shows a gas sensor equipped with a protective cover assembly according to the first embodiment of the invention.

Referring to the drawings, wherein like reference numbers refer to like parts in several views, particularly to FIG. 1, there is shown a gas sensor 1 according to the first embodiment of the invention which may be employed in a burning control system for automotive engines to measure the concentration of a gas component such as $O_2$ or NOx contained in exhaust gasses of the engine.

The gas sensor 1 generally includes a gas sensor element 15, a first insulation porcelain 12, a second insulation porcelain 13, a hollow cylindrical housing 10, an air cover 11, and a protective cover assembly 2. The gas sensor element 15 is made of a laminated plate made up of a base portion and a sensing portion exposed directly to a gas to be measured. For example, U.S. Pat. No. 5,573,650, issued on Nov. 12, 1996 to Fukaya et al. teaches a typical laminated sensor element, the disclosure of which is incorporated herein by reference. The gas sensor element 15 is retained within the housing 10 and has a given length extending in a longitudinal center line of the gas sensor 1.

The first insulation porcelain 12 is fitted within the housing 10 and holds therein the gas sensor element 15. The second insulation porcelain 13 is mounted on the first insulation porcelain 12 in alignment with each other and surrounds the base portion of the gas sensor element 15. The air cover 11 is installed at an end thereof on the housing 10 to cover the second insulation porcelain 13.

The cover assembly 2 is installed in a head of the housing and has a length extending in alignment with the longitudinal center line of the gas sensor 1 (i.e., the gas sensor element 15). The cover assembly 2 consists of an outer cover 21 and an inner cover 22 and has a flange (will also be referred to as a base below) installed on the end wall 101 of the housing 10 to define a gas chamber 200 within which the sensing portion of the gas sensor element 15 is disposed and into which a gas to be measured is admitted through gas inlet holes 210 and 220 formed in the outer and inner covers 21 and 22, respectively. The gas inlet holes 220 are located closer to the base portion of the gas sensor element 15 (i.e., an upper portion as viewed in FIG. 1) than the gas inlet holes 210.

Figure 2:
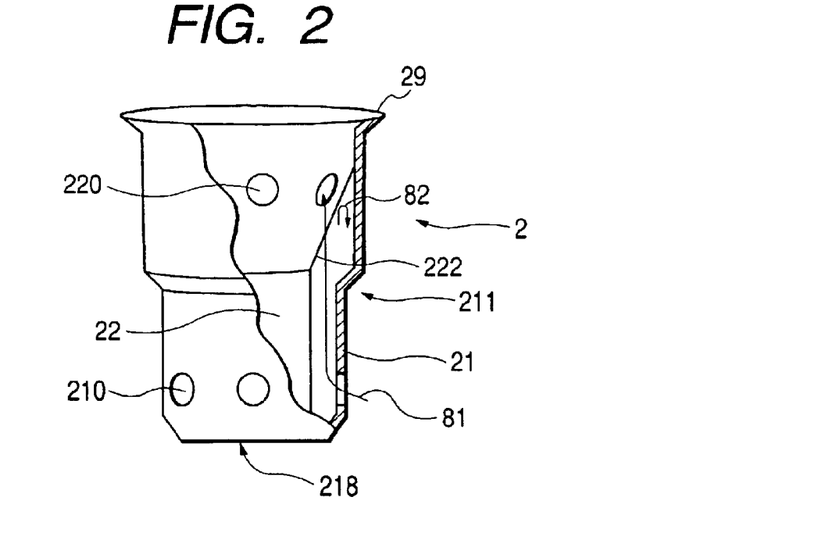
FIG. 2 is a partially sectional view which shows an internal structure of the protective cover assembly in FIG. 1.
Figure 3:
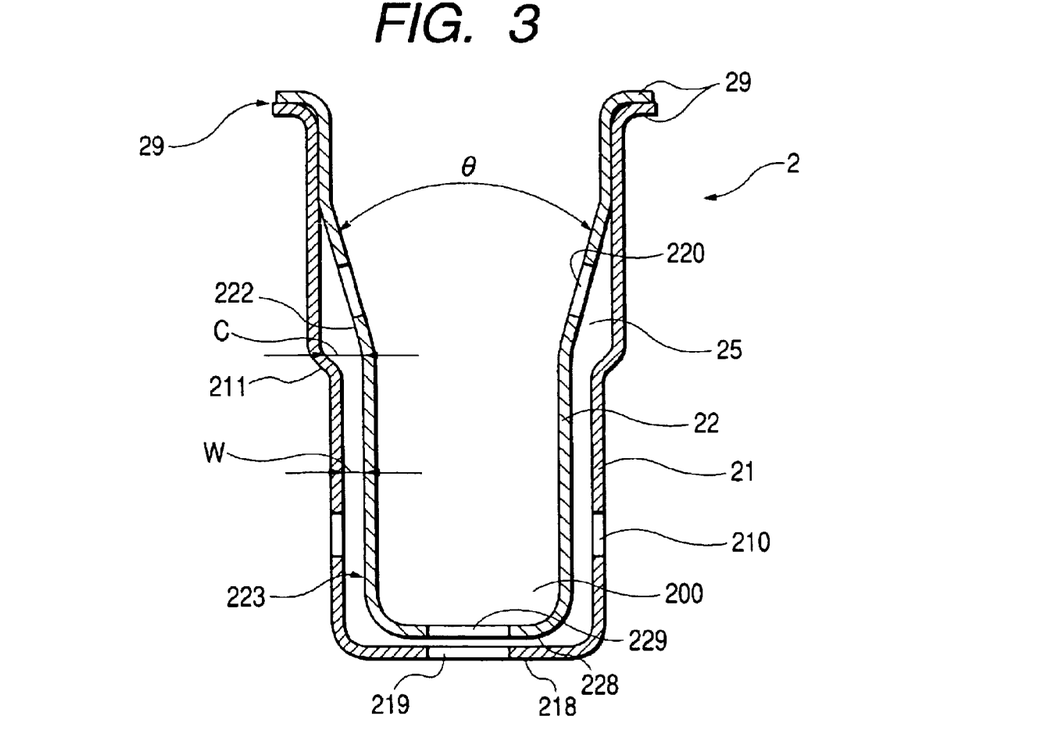
FIG. 3 is a longitudinal sectional view which shows the protective cover assembly of FIG. 2.

The inner cover 22 is disposed within the outer cover 21 to define a clearance 25, as shown in FIG. 3, between an inner wall of the outer cover 21 and an outer wall of the inner cover 22. The clearance 25 defines a gas path which extends substantially in the longitudinal direction of the gas sensor 1 and establishes a gas flow 81, as shown in FIG. 2, directed from the gas inlet holes 210 into the gas chamber 200 through the gas inlet holes 220. The gas flow 81, as described in the introductory part of this application, forms a return flow 82, as shown in FIG. 2, from an upper end of the clearance 25 which disturbs the entrance of the gas flow 81 into the gas chamber 200 through the gas inlet holes 220, but however, the structure of the cover assembly 2 of this embodiment is designed to alleviate such a problem, as discussed below in detail.

The outer cover 21 of the cover assembly 2 has formed thereon, as clearly shown in FIG. 2, a shoulder 211 tapering toward the bottom of the cover assembly 2 (i.e., a lower portion, as viewed in the drawing). The inner cover 22 has a tapered wall 222 which extends inward and downward from a portion thereof closer to the base of the cover assembly 2 than the shoulder 211 of the outer cover 21. The inner cover 22 has the gas inlet holes 220 formed in the tapered wall 222.

The following discussion will refer to an example in which the gas sensor 1 is used for burning control of an automotive internal combustion engine.

The housing 10 is made of a metallic cylinder installed on an exhaust pipe of the engine to have the cover assembly 2 exposed to exhaust emissions. The first insulation porcelain 12 is fitted within the housing 10 hermetically and retains therein the gas sensor element 15 in an air-tight fashion using a sealing member 121 made of a glass material, for example.

The second insulation porcelain 13 is made of a hollow cylindrical insulating member and disposed within the air cover 11. The second insulation porcelain 13 surrounds the base portion of the gas sensor element 15 and has disposed therein four leads 131 (only two are shown for the simplicity of illustration) each of which is made of a wire folded elastically to make an electric contact at one end with an electrode terminal (not shown) formed on the gas sensor element 15. The leads 131 extend at the other end through holes formed in an end of the second insulation porcelain 13 and connect with leads 142 through connectors 141, respectively, for transmission of sensor signals between the gas sensor element 15 and an external device and supply of electric power to a heater installed on the gas sensor element 15.

The air cover 11 is, as described above, fitted on the boss of the housing 10. An outer cover 113 is provided around the air cover 11 and staked or crimped to retain a water-repellent filter 112 on the periphery of the air cover 11. The air cover 11 and the outer cover 113 have formed therein air inlets 115 through which air is admitted as a reference gas into an air chamber 110 defined between the bottom of the insulating holder 16 and the base end of the second insulation porcelain 13.

The cover assembly 2, as already discussed, is made up of the outer and inner covers 21 and 22. The outer and inner covers 21 and 22 are, as clearly shown in FIGS. 2 and 3, made of hollow cylinders which have gas holes 219 and 229 formed in bottoms 218 and 228, respectively. The gas inlet holes 210 are formed at regular intervals in a peripheral wall of the outer cover 21 and at the same level from the bottom 218. The gas inlet holes 210 are circular and have substantially the same diameter. Similarly, the gas inlet holes 220 are formed at regular intervals in a peripheral wall of the inner cover 22 and at the same level from the bottom 228. The gas inlet holes 220 are circular and have substantially the same diameter.

The outer and inner covers 21 and 22 have flanges 29 which are fitted in an annular groove 102, as shown in FIG. 1, formed in the end wall 101 of the housing 10. The outer cover 21, as described above, has the shoulder 211 formed on a central peripheral wall thereof which is located closer to the flange 29 than the gas inlet holes 210.

The inner cover 22, as clearly shown in FIG. 3, has the tapered wall 222 and a straight cylinder 223. The tapered wall 222 extends beneath the flange 29 inward and downward and terminates at a location closer to the base of the cover assembly 2 than the shoulder 211 of the outer cover 21. The straight cylinder 223 extends straight from the tapered wall 222 to the bottom 228 substantially in parallel to the longitudinal center line of the gas sensor 1. The gas inlet holes 220 are formed in the tapered wall 222. Specifically, the gas inlet holes 220 are oriented upstream of the gas flow 81 for facilitating ease of the entrance of the gas flow 81 into the gas chamber 200.

The interval W between an outer surface of the straight cylinder 223 of the inner cover 22 and an inner surface of the outer cover 21 is 0.9 mm. The angle θ defined between diametrically opposed portions of the tapered wall 222 of the inner cover 22 is 30°.

The interval C between a downstream end of an inner surface of the shoulder 211 (i.e., an upper end of the shoulder 211, as viewed in FIG. 3) and an opposite portion of the outer surface of the inner cover 22 in a direction traversing the longitudinal center line of the gas sensor 1 is set greater than the interval W (C>W). For instance, the interval C is 1.5 mm which is greater than the interval W of 0.9 mm. Specifically, a downstream portion of the gas path (i.e., the clearance 25) near the gas inlet holes 220 of the inner cover 22 is greater in sectional area than an upstream portion of the gas path near the gas inlet holes 210 of the outer cover 21. This structure serves to define along a portion of the inner wall of the outer cover 21 above the shoulder 21 1 an outer gas path through which the return flow 82 passes without interfering the gas flow 81 entering the gas inlet holes 220 of the inner cover 22, thereby preventing the return flow 82 from disturbing the entrance of the gas flow 81 into the gas chamber 200 through the gas inlet holes 220, which is objectionable in a conventional structure such as the one shown in FIGS. 16 and 17.

We carried out tests, as discussed below, on the gas sensor 1 of this embodiment to evaluate the performance of the cover assembly 2.

Figure 4:
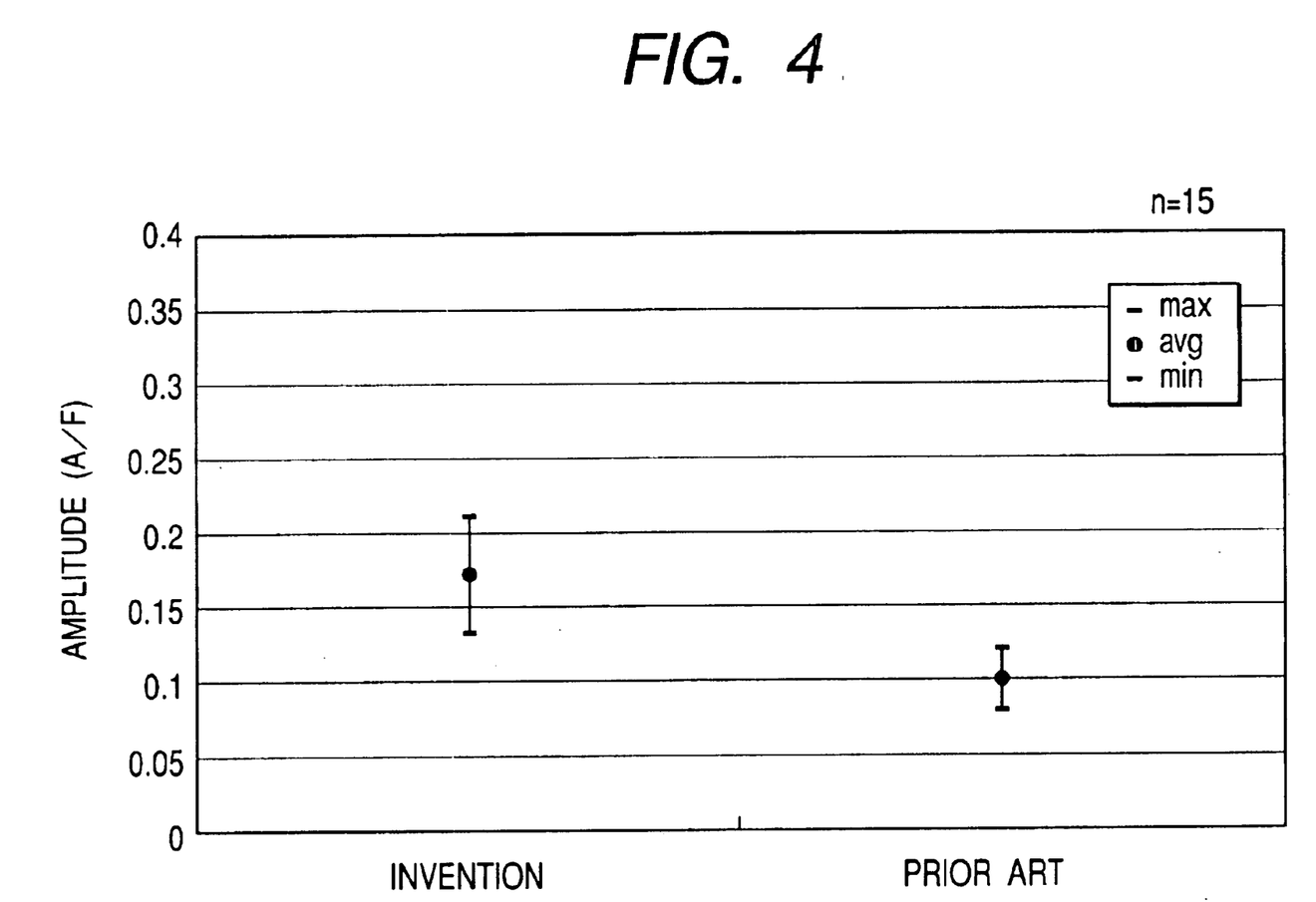
FIG. 4 is a graph which represents a comparison between response rates of a gas sensor of the first embodiment and a conventional gas sensor.

We supplied a mixture having an air-fuel ratio of 14:5 to three of four cylinders of an internal combustion engine and a mixture 10% richer in air-fuel ratio than that mixture to a remaining one of the cylinders, thereby changing the concentration of oxygen contained in exhaust emissions from the engine cyclically. We installed the gas sensor 1 in an exhaust pipe of the engine and exposed the cover assembly 2 to the exhaust emissions to determine the air-fuel ratio. An output of the gas sensor 1 varied as a function of a cyclic change in concentration of oxygen contained in the exhaust emissions. The degree of response of the gas sensor 1 to a change in concentration of oxygen may be expressed as a function of the amplitude of the sensor output. Specifically, when the degree of response is higher, it will cause the amplitude of the sensor output to increase, while when the degree of response is lower, it will cause the amplitude to decrease. We, thus, measured the amplitude of an output of the gas sensor 1 fifteen times and evaluated the degree of response of the gas sensor 1. We also carried out the same performance test on a conventional gas sensor of the type, as shown in FIGS. 16 and 17, in which the outer and inner covers 91 and 92 both have straight inner walls spaced at the interval W of 1.0 mm. The test results are shown in FIG. 4. Black circles represent average values of measured amplitudes of the outputs of the gas sensor 1 of this embodiment and the conventional gas sensor. The graph of FIG. 4 shows that the average value of the output of the gas sensor 1 lies near 0.17 A/F, while the average value of the output of the conventional gas sensor lies near 0.1 A/F, and that the output of the gas sensor 1 is 1.7 times greater in amplitude than that of the conventional gas sensor and excellent in response to a change in concentration of a gas to be measured.

The cover assembly 2 of this embodiment is, as described above, designed to minimize the adverse effect of the return flow 82 on the gas flow 81 within the clearance 25 between the outer and inner covers 21 and 22. Specifically, the cover assembly 2 has the shoulder 211 formed on the side wall of the outer cover 21 to define a wider portion of the clearance 25 on a downstream side of the gas path near the gas inlet holes 220 of the inner cover 22, thereby forming the outer gas path in the wider portion of the clearance 25 through which the return flow 82 passes without interfering the gas flow 81 entering the gas inlet holes 220 of the inner cover 22. This prevents the return flow 82 from disturbing the entrance of the gas flow 81 into the gas chamber 200 through the gas inlet holes 220. Additionally, the tapered wall 222 of the inner cover 22 also serve to facilitates the direct entrance of the gas flow 81 into the gas inlet holes 220 of the inner cover 22.

Figure 5:
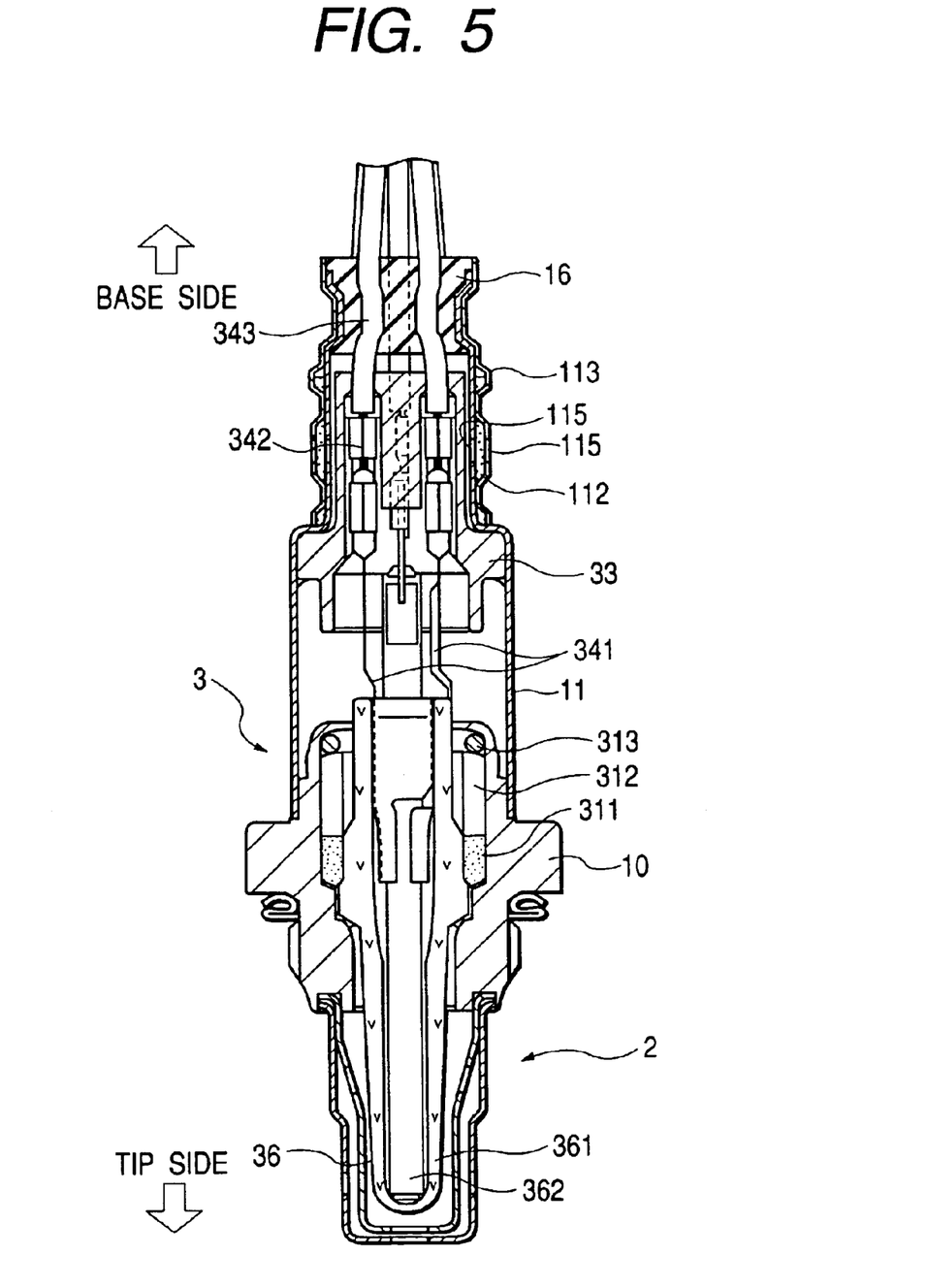
FIG. 5 is a longitudinal sectional view which shows another type of gas sensor in which a protective cover assembly of this invention may be mounted.

The cover assembly 2 of this embodiment is installed in the gas sensor 1 having the gas sensor element 15 made of, as described above, a laminated plate, but however, it may be installed, as shown in FIG. 5, a gas sensor 3 having a cup-shaped gas sensor element 36. The gas sensor element 36 is retained within the housing 10 hermetically through a powder seal 311, a glass insulator 312, and a metallic ring 313. The metallic ring 313 is pressed downward, as viewed in the drawing, by bending an annular end of the housing 10 inward.

The gas sensor element 36 consists of a cup-shaped solid electrolyte body 361 and a bar heater 362 installed within the solid electrolyte body 361. The gas sensor element 36 connects electrically with leads 341 which are coupled to leads 343 through connectors 342 mounted in a porcelain insulator 33 fitted within the air cover 11.

Figure 6:
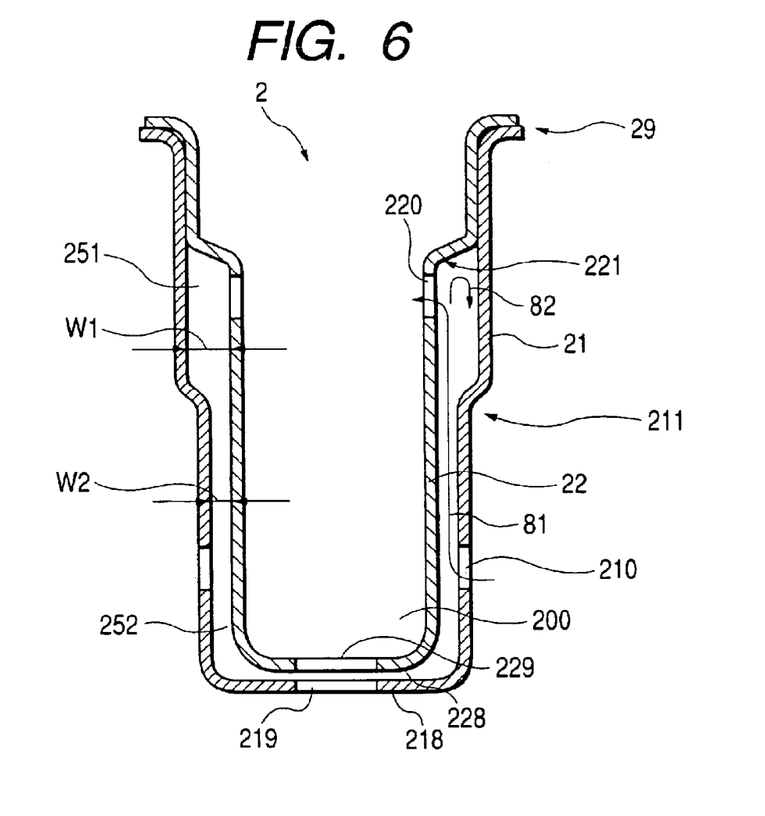
FIG. 6 is a longitudinal sectional view which shows an internal structure of a protective cover assembly according to the second embodiment of the invention.

FIG. 6 shows the cover assembly 2 according to the second embodiment of the invention.

The inner cover 22 has a shoulder 221 located above the shoulder 211 of the outer cover 21, as viewed in the drawing, to define a wider clearance W1 and a narrower clearance W2 between the inner walls of the outer and inner covers 21 and 22. The wider clearance W1 is preferably 1.1 times greater than the clearance W2 or more. For instance, the wider clearance W1 is 1.5 mm. The narrower clearance W2 is 0.9 mm. The inlet holes 220 of the inner cover 22 are formed immediately beneath the shoulder 221. With this structure, the part of the gas flow 81 not admitted into the inlet holes 220 reflects on the surface of the shoulder 221 to form the return flow 82 oriented downward, as viewed in the drawing, along the inner wall of the outer cover 21 above the shoulder 211. Specifically, the gas flow 81 and the return flow 82 pass at a relatively greater interval away from each other within the wider clearance W1, thereby minimizing the interference of the return flow 82 with the gas flow 81 entering the gas chamber 200 through the inlet holes 220.

Other arrangements are identical with those in the first embodiment, and explanation thereof in detail will be omitted here.

Figure 7:
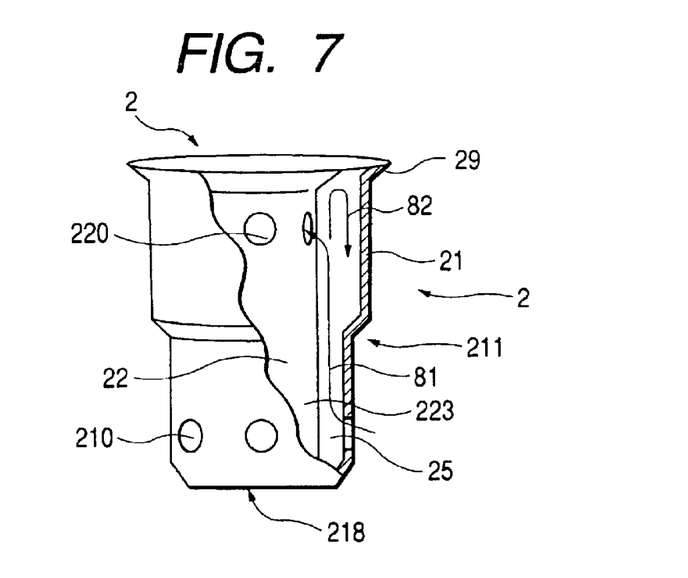
FIG. 7 is a partially sectional view which shows an internal structure of a protective cover assembly according to the third embodiment of the invention.

FIG. 7 shows the cover assembly 2 according to the third embodiment of the invention.

The inner cover 22 does not have any shoulder and has a straight outer wall 223 extending straight from the flange 29 in the longitudinal direction of the gas sensor 1. This structure, like the second embodiment, define a wider and a narrower clearance, thereby decreasing the interference of the return flow 82 with the gas flow 81 entering the inlet holes 220. Other arrangements are identical with those in the first embodiment, and explanation thereof in detail will be omitted here.

Figure 8:
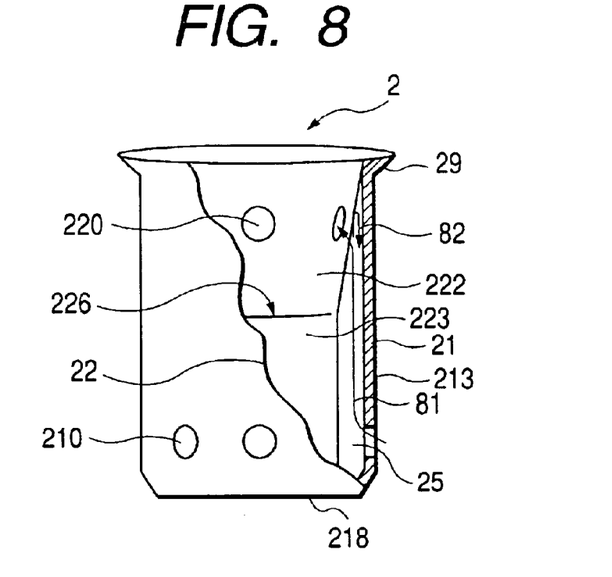
FIG. 8 is a partially sectional view which shows an internal structure of a protective cover assembly according to the fourth embodiment of the invention.

FIG. 8 shows the cover assembly 2 according to the fourth embodiment of the invention.

The inner cover 22 has, like the first embodiment, the tapered wall 222 formed immediately beneath the flange 29, while the outer cover 21 has a straight cylinder 213 which extends straight from the flange 29 toward the bottom 218 and has a constant diameter. The tapered wall 222 extends from the flange 29 to a central peripheral portion 226 of the inner cover 22. A lower portion of the inner cover 22 below the central peripheral portion 226 extends straight to define a substantially constant clearance between itself and the outer cover 21. Other arrangements are identical with those in the first embodiment, and explanation thereof in detail will be omitted here.

The gas flow 81 enters the inlet holes 220 along the tapered wall 222. The part of the gas flow 81 not admitted into the inlet holes 220 forms the return flow 82 passing outside the gas flow 81, thereby decreasing the interference of the return flow 82 with the gas flow 81 entering the inlet holes 220.

The tapered wall 222 also serves to decrease the volume of the clearance 25 gradually as reaching the base of the cover assembly 2, thereby resulting in an increase in velocity of the gas flow 81 entering the inlet holes 220.

Figure 9:
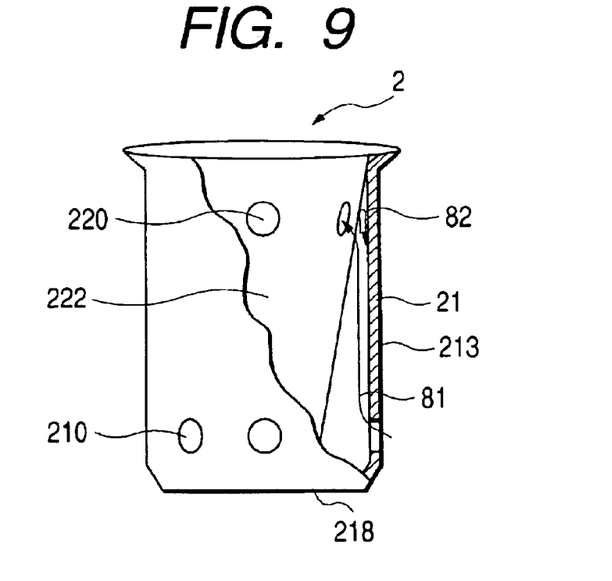
FIG. 9 is a partially sectional view which shows an internal structure of a protective cover assembly that is a modification of the one shown in FIG. 8.

The tapered wall 222 may alternatively be formed, as shown in FIG. 9, which extends to the bottom of the inner cover 22.

Figure 10:
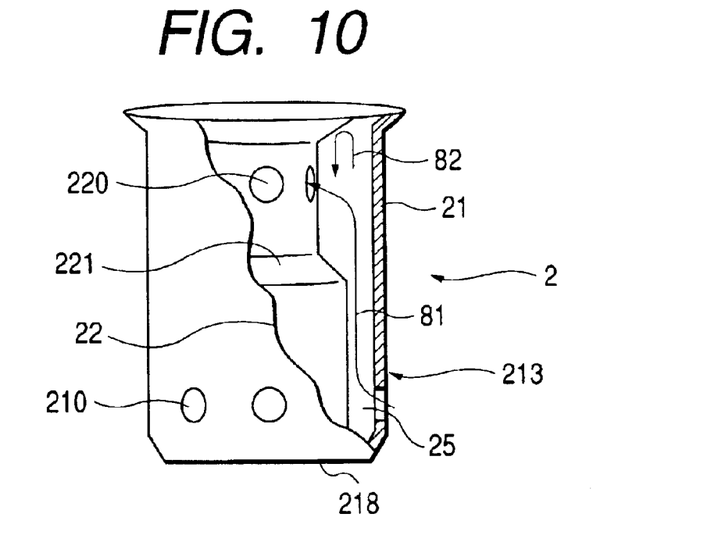
FIG. 10 is a partially sectional view which shows an internal structure of a protective cover assembly according to the fifth embodiment of the invention.

FIG. 10 shows the cover assembly 2 according to the fifth embodiment of the invention.

The outer cover 21, like the fourth embodiment of FIG. 8, has the straight cylinder 213 having a constant diameter, while the inner cover 22 has a shoulder 221 to define a wider annular clearance and a narrower annular clearance between the outer and inner covers 21 and 22. The inlet holes 220 are formed in a small-diameter portion of the inner cover 22 above the shoulder 221.

The gas flow 81 enters the inlet holes 220 within the wider clearance, thereby decreasing the interference of the return flow 82 with the gas flow 81 entering the inlet holes 220.

Other arrangements and operation are identical with those in the first embodiment, and explanation thereof in detail will be omitted here.

Figure 11:
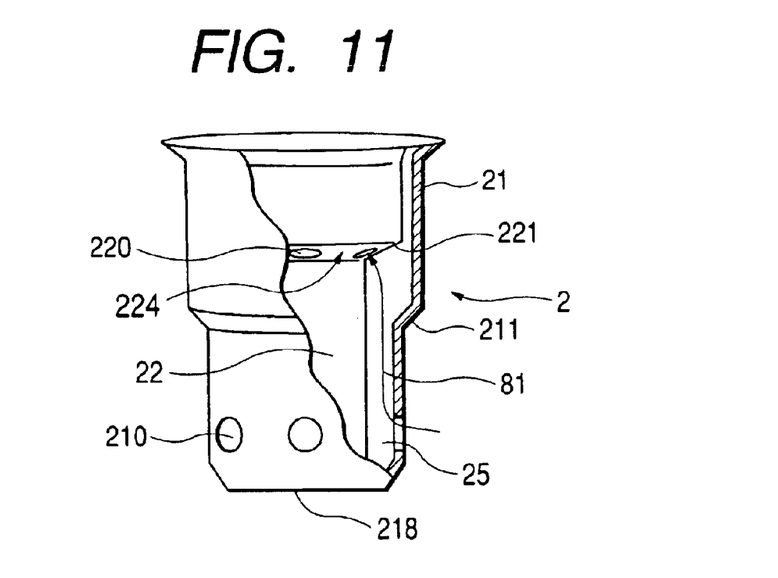
FIG. 11 is a partially sectional view which shows an internal structure of a protective cover assembly according to the sixth embodiment of the invention.

FIG. 11 shows the cover assembly 2 according to the sixth embodiment of the invention.

The outer cover 21 has, like the first embodiment, the shoulder 211. The inner cover 22 has, like the second embodiment, the shoulder 221, but has formed in a peripheral wall 224 of the shoulder the inlet holes 220 oriented downward to the inlet holes 210 of the outer cover 21, thereby facilitating direct entrance of the gas flow 81 into the inlet holes 220 of the inner cover 22, which hardly induces a return flow oriented downward to the inlet holes 210.

Other arrangements and operation are identical with those in the first embodiment, and explanation thereof in detail will be omitted here.

Figure 12:
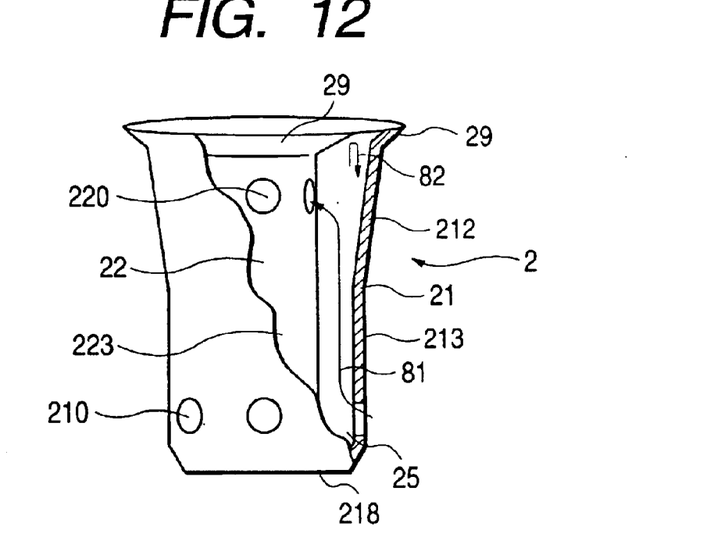
FIG. 12 is a partially sectional view which shows an internal structure of a protective cover assembly according to the seventh embodiment of the invention.

FIG. 12 shows the cover assembly 2 according to the seventh embodiment of the invention.

The outer cover 21 includes a tapered wall 212 extending from the flange 29 to a middle portion thereof and the straight wall 213 extending from the middle portion to the bottom 218. The inner cover 22 includes the straight cylinder 223 extending from the flange 29 to the bottom thereof, thereby defining a wider clearance around the inlet holes 220 of the inner cover 22, which reduces the interference of the return flow 82 with the gas flow 81 entering the inlet holes 220.

Other arrangements and operation are identical with those in the first embodiment, and explanation thereof in detail will be omitted here.

Figure 13:
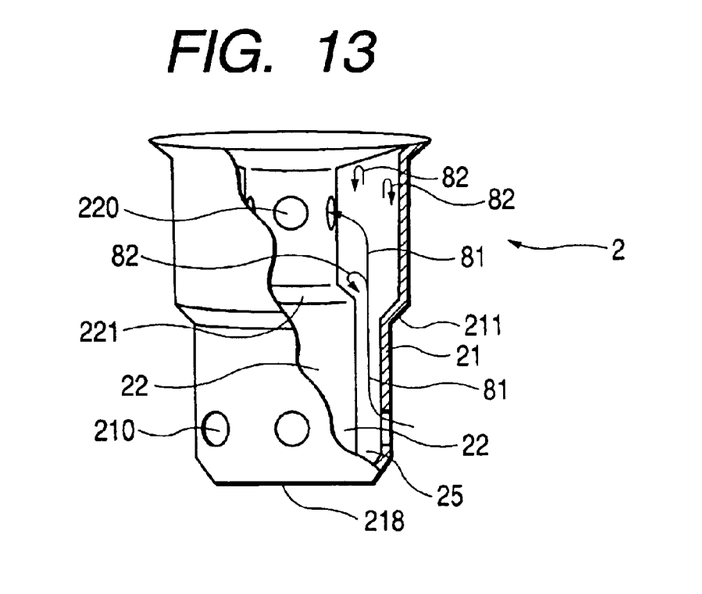
FIG. 13 is a partially sectional view which shows an internal structure of a protective cover assembly according to the eighth embodiment of the invention.

FIG. 13 shows the cover assembly 2 according to the eighth embodiment of the invention which is a combination of the first embodiment and the fifth embodiment of FIG. 10.

The outer cover 21 has the shoulder 211 extending upward and outward, while the inner cover 22 has the shoulder 221 extending upward and inward, thereby defining a wider annular clearance around the inlet holes 220 of the inner cover 22. The inlet holes 220 are formed in a small-diameter portion of the inner cover 22.

The wider clearance defined between the inner cover 22 and the outer cover 21 around the inlet holes 220 works to increase intervals between the gas flow 81 entering the inlet holes 220 and the return flows 82, thereby decreasing the interference of the return flows 82 with the gas flow 81 entering the inlet holes 220.

Other arrangements and operation are identical with those in the first embodiment, and explanation thereof in detail will be omitted here.

Figure 14:
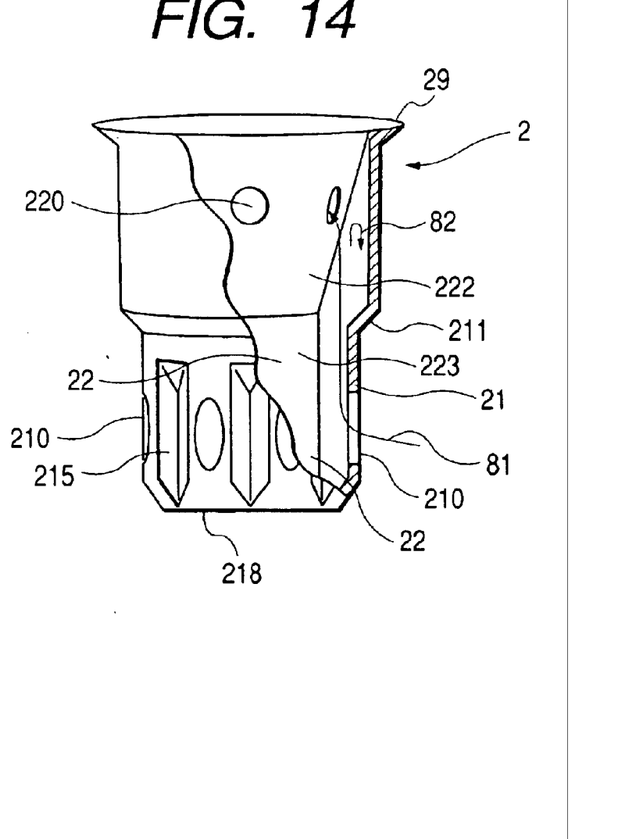
FIG. 14 is a partially sectional view which shows an internal structure of a protective cover assembly according to the ninth embodiment of the invention.
Figure 15:
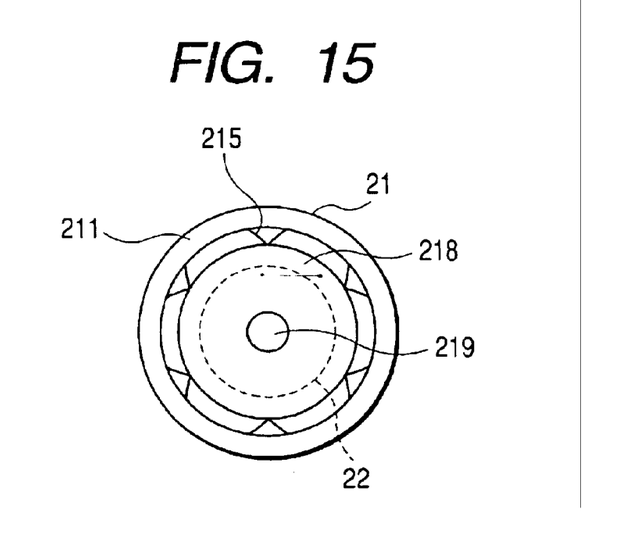
FIG. 15 is a bottom view which shows grooves formed in a side wall of an outer cover of the cover assembly of FIG. 14.

FIGS. 14 and 15 show the cover assembly 2 according to the ninth embodiment of the invention.

The outer cover 21 has, like the first embodiment, the shoulder 211 extending upward and outward. The inner cover 22 has, like the fourth embodiment of FIG. 8, the tapered wall 222 extending from the flange 29 in which tapered wall 222 the inlet holes 220 are formed and oriented downward to the inlet holes 210 of the outer cover 21.

The outer cover 21 has formed beneath the shoulder 211 six oval inlet holes 210 elongated in the longitudinal direction of the cover assembly 2. The oval inlet holes 210 are arranged at regular intervals around the periphery of the inner cover 22. Between adjacent two of the oval inlet holes 210, a V-shaped groove 215 is, as clearly shown in FIG. 15, formed in an outer wall of the outer cover 21 which projects inward. Other arrangements are identical with those in first embodiment, and explanation thereof in detail will be omitted here.

The tapered wall 222 of the inner cover 22 and the shoulder 211 of the outer cover 21 define a wider annular clearance tapering off to the inlet holes 220, thereby facilitating direct entrance of the gas flow 81 to the inlet holes 220 and causing the return flow 82 to be oriented downward along the inner wall of the outer cover 21, which decreases the interference of the return flows 82 with the gas flow 81 entering the inlet holes 220. Each of the V-shaped grooves 215 preferably extends in alignment with one of the inlet holes 220 of the inner cover 22 so that it works to orient the gas flow 81 directly to the one of the inlet holes 220, thereby facilitating the entrance of the gas flow 81 thereinto.

The V-shaped grooves 215 may also be provided in any of the above described first to eighth embodiments.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor having a length with a first and a second end opposed to each other comprising:

a hollow cylindrical housing having a first end and a second end respectively adjacent the first and second ends of the gas sensor;

a sensing element retained within said housing which has a length extending in a longitudinal direction of the gas sensor, including a sensing portion working to measure a concentration of a specified gas; and a cover assembly installed on the second end of said housing to define a gas chamber in which the sensing portion of said sensing element is disposed and into which the specified gas is admitted, said cover assembly having a length extending in the longitudinal direction of the gas sensor, including an outer and an inner cover, the outer cover having a first gas inlet hole formed in a side wall thereof, the inner cover having formed in a side wall thereof a second gas inlet hole which is located closer to the first end of the gas sensor than the first gas inlet hole of the outer cover, the inner cover being disposed within the outer cover with a given clearance between the outer and inner covers, wherein one of the outer and inner covers of said assembly has formed on the side wall thereof a shoulder which separates the clearance between the outer and inner covers into a wider and a narrower portion, and wherein the wider portion is located nearer the second gas inlet hole of the inner cover than the narrow portion.

2. A gas sensor as set forth in claim 1, wherein the wider portion is 1.1 times wider than the narrower portion.

3. A gas sensor as set forth in claim 1, wherein the inner cover has a gas flow-intercepting wall that is disposed at an angle to a gas flow direction from said first gas inlet hole to said second gas inlet hole, the second gas inlet hole being formed in the gas flow-intercepting wall.

4. A gas sensor as set forth in claim 3, wherein the gas flow-intercepting wall is defined by a shoulder which is formed on the side wall of the inner cover and flares outward and toward the first end of the gas sensor.

5. A gas sensor as set forth in claim 1, further comprising a groove formed in the side wall of the outer cover serving to direct the flow of the specified gas toward the second gas inlet hole of the inner cover.

6. A gas sensor as set forth in claim 1, wherein
the inner cover has a tapered surface formed on a side wall thereof.

7. A gas sensor as set forth in claim 6, wherein the inner cover has a straight surface continuing from the tapered surface, extending straight in the longitudinal direction of the gas sensor.

8. A gas sensor as set forth in claim 6, further comprising a groove formed in the side wall of the outer cover serving to direct the flow of the specified gas toward the second gas inlet hole of the inner cover.

9. A gas sensor as set forth in claim 6, wherein the outer cover has said shoulder formed closer to an upstream side of the flow of the specified gas than the tapered surface of the inner cover to define an upstream portion of the gas path closer to the first gas inlet hole of the outer cover and a downstream portion of the gas path closer to the second gas in let hole of the inner cover, the downstream portion being greater in area than the upstream portion in a direction traversing the longitudinal direction of the gas sensor.

10. A gas sensor as set forth in claim 6, wherein the outer cover has formed on the side wall thereof said shoulder, said shoulder being tapered to define the wider portion of the clearance between the tapered surface of the inner cover and the shoulder of the outer cover, and further comprising a groove formed in a portion of the side wall of the outer cover closer to the first gas inlet hole than the shoulder of the outer cover, the groove serving to direct the flow of the specified gas toward the second gas inlet hole of the inner cover.

11. A gas sensor as set forth in claim 10, wherein the groove has a length extending in alignment with the second gas inlet hole of the inner cover in the longitudinal direction of the gas sensor.

12. A gas sensor as set forth in claim 6, wherein the inner cover has formed in the tapered surface thereof said second gas inlet hole.

* * * * *